(12) United States Patent
Gallagher

(10) Patent No.: US 6,813,935 B2
(45) Date of Patent: Nov. 9, 2004

(54) MECHANICAL RESONATOR SYSTEM

(76) Inventor: John G Gallagher, 77 Town Street, Old Malton, North Yorkshire (GB), YO17 0DH ( * ) Notice: Subject to any disclaimer, the term of this patent is extended or adjusted under 35 U.S.C. 154(b) by 0 days.

(21) Appl. No.: 10/382,101

(22) Filed: Mar. 6, 2003

(65) Prior Publication Data
US 2003/0167829 A1 Sep. 11, 2003

(30) Foreign Application Priority Data
Mar. 6, 2002 (GB) .............................. 0205228

(51) Int. Cl.[7] .................. G01N 11/10; G01N 11/14
(52) U.S. Cl. ............................... 73/54.24; 73/54.28
(58) Field of Search ..................... 73/54.24–54.34, 73/32 A

(56) References Cited

U.S. PATENT DOCUMENTS

| | | | | |
|---|---|---|---|---|
| 1,912,343 A | * | 5/1933 | Buckingham | ............... 84/457 |
| 1,913,331 A | * | 6/1933 | Buckingham | ............... 84/733 |
| 2,179,828 A | * | 11/1939 | Park | ............... 434/367 |
| 3,382,706 A | * | 5/1968 | Fitzgerald et al. | ......... 73/54.25 |
| 4,312,217 A | * | 1/1982 | Hartert | ............ 73/64.42 |
| 4,811,593 A | * | 3/1989 | Miura et al. | ............ 73/54.26 |
| 4,909,068 A | * | 3/1990 | Miura et al. | ............... 73/32 A |
| 5,596,139 A | * | 1/1997 | Miura et al. | ............ 73/54.24 |
| 5,763,766 A | * | 6/1998 | Robinson | ............... 73/54.33 |
| 6,194,817 B1 | * | 2/2001 | Yachi et al. | ............... 310/370 |

FOREIGN PATENT DOCUMENTS

GB    2099998 A    * 12/1982

OTHER PUBLICATIONS

SU–396590A, Derwent Abstract.*

* cited by examiner

Primary Examiner—Michael Cygan
(74) Attorney, Agent, or Firm—Nixon & Vanderhye, PC

(57) ABSTRACT

A mechanical resonator system such as a vibrational viscometer includes two distinct resonators, connected by a nexus. The system is capable of vibration in anti-phase with a first vibrational node in the region of the nexus and at least a second node. A compliant support is provided in the region of the first node and a semi-rigid support in the region of the second node.

5 Claims, 2 Drawing Sheets

TORSIONAL RESONATOR SCHEMATIC
*(Prior Art)*

CASE 1 - TORSIONAL RESONATOR

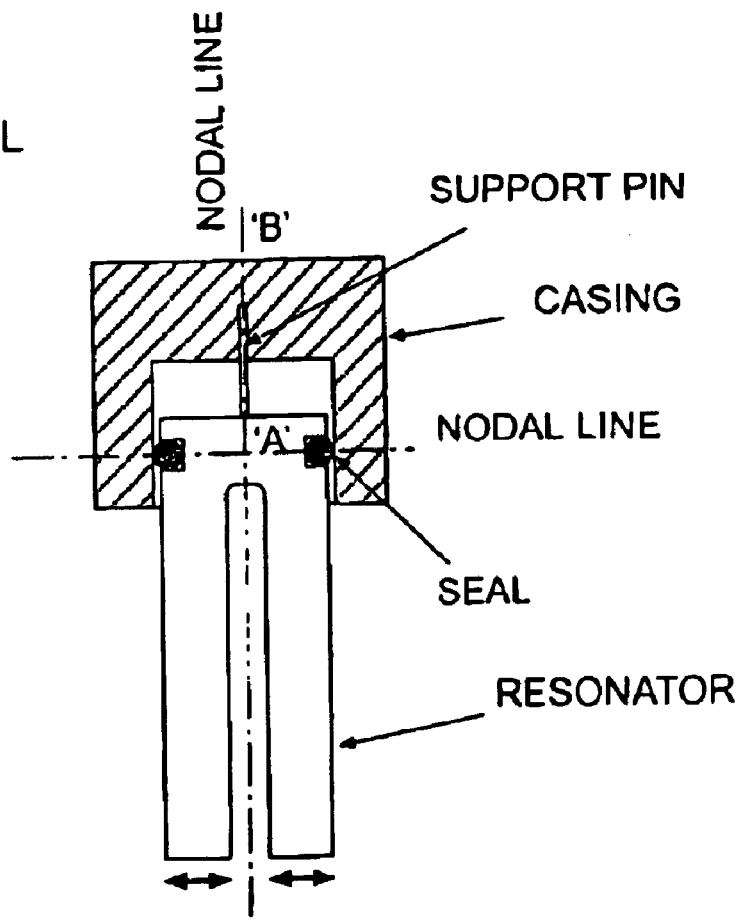

MECHANICAL RESONATOR SYSTEM

FIELD OF THE INVENTION

The present invention relates to mechanical resonators and measuring instruments, such as viscometers or other instruments for measuring attributes of materials such as fluid media

BACKGROUND TO THE INVENTION

FIG. 1 shows a torsional resonant system consisting of two distinct but connected resonators; one resonator is formed by an inertial mass J1 and its associated shaft K1 and the other formed by an inertial mass J2 and its shaft K1. The two shafts are connected at their ends so that, when the resonators are tuned to the same frequency, a vibrational node is formed at the shafts' junction, In a practical arrangement it is necessary to physically support the resonator system in space. To prevent damping of the moving members, the most appropriate point of support is at any vibrational nodal position where there is zero or minimal displacement in resonance. Conventionally, a single support structure K3 is located at the junction of the two shafts as shown schematically in FIG. 1. However, if there is a slight imbalance of frequencies between the two resonator systems then there will be some displacement at the node and the rigidity of the support structure will influence the resonant characteristics of the overall system. Although frequency imbalance may be naturally expected to occur the complex involvement of mounting rigidity is undesirable.

Reducing the mounting stiffness by using a more compliant design and/or materials will diminish the effect of the stiffness of the structure K3 (as described in GB-2281621) but compromises structural strength and thus significantly limits practical use. This invention describes a resonator support structure which has the virtues of high compliance to virtually eliminate detrimental effects of K3 but to preserve structural strength for practical usage.

SUMMARY OF THE INVENTION

According to the invention a mechanical resonator system comprises two distinct resonators connected by a nexus and being capable of vibration in anti-phase with a first vibrational node in the region of the nexus and at least a second node, a compliant support in the region of the first node and a semi-rigid support in the region of the second node. Further features of the invention will be apparent from the following description of an exemplary embodiment.

BRIEF DESCRIPTION OF THE DRAWINGS

FIG. 3 illustrates another resonator according to the invention

DETAILED DESCRIPTION

Figure 1:
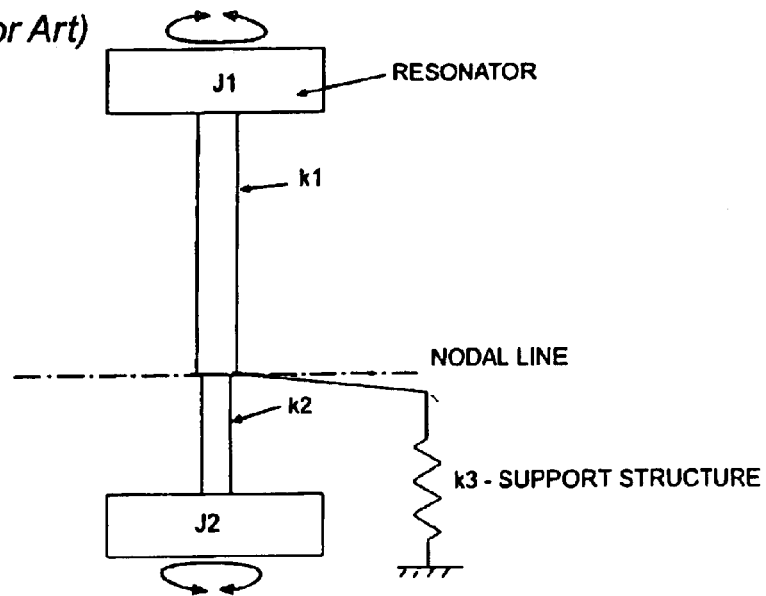
FIG. 1 illustrates a known form of resonator system
Figure 2:
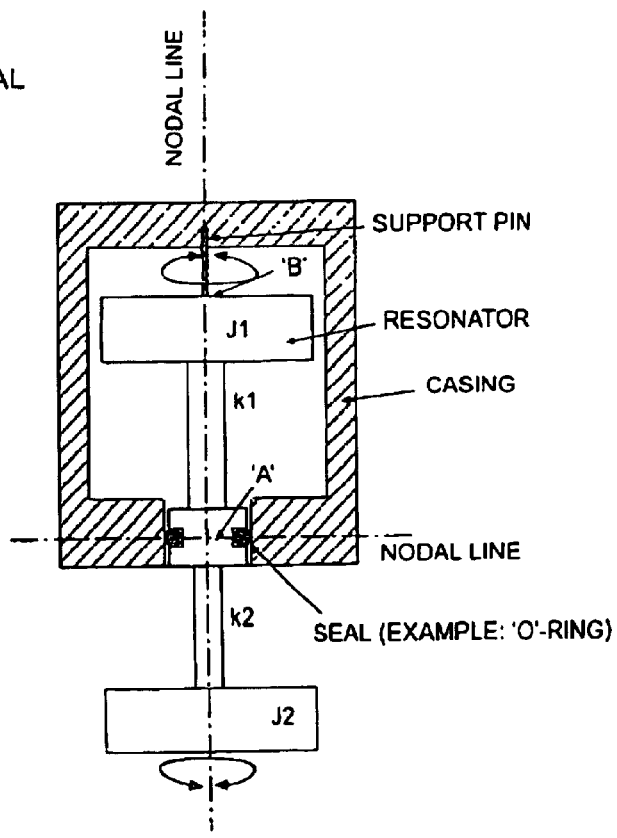
FIG. 2 illustrates a resonator according to the invention.

The basis of this invention is to support the resonator structure at two points rather than one. Many vibrating systems have more than one nodal region and this is shown in FIGS. 2 and 3 by way of example. Using the torsional model shown in FIG. 2 the invention is described as follows:

FIG. 2 shows a torsional resonant system consisting of two separate resonators; one resonator is formed by an inertial mass J1 and it associated shaft K1 with the other formed by an inertial mass J2 and its shaft K2. The two shafts are connected at their ends so that, when the resonator is tuned to the same frequency a vibrational node is formed at the shaft junction. A second vibrational node is formed at the axis of angular displacement which runs the length of the resonator structure.

In practical usage, for example as a viscometer, it is desirable to expose one part of the resonator to a fluid and use the other part for electromechanical stimulation and sensing. For these purposes the inertial mass J1 may be associated with an electromagnetic drive and a sensing circuit as described for example in my U.S. Pat. Nos. 6,450,013, 5,363,691 and 5,670,709, all of which are incorporated herein by reference, U.S. Pat. No. 3,712,117 (Fitzgerald) and elsewhere. The stimulation preferably produces anti-phase resonance of the two inertial masses. Such an arrangement usually requires a seal separating one system from the other and this is preferably located at the node formed by the nexus of the two anti-vibrating shafts, and shown as 'A'. The seal is designed to be compliant and can be formed from 'O-rings' in a piston-seal configuration or any other similar arrangement using compliant materials, for example, the seal can be formed using any low rigidity structure such as a metallic torsional spring section.

On its own, such high compliance at this point would give low structural strength. Therefore, in order to provide rigidity a second member is disposed between the node of angular displacement and the casing, and shown as 'B' in FIG. 2. In particular the pin engages the upper inertial mass where the nodal line intersects the upper inertial mass J1. This member is 'semi-rigid' in that it has low torsional rigidity to allow free torsional vibration but high longitudinal and lateral rigidity to provide structural strength in combination with the seal structure. Such a member can be realized as a narrow column, or pin, which is torsionally compliant by virtue of its narrow diameter but is sufficiently short in length to simultaneously provide rigidity to resist the longitudinal forces due to pressure and accelerations in the Y plane, and lateral forces in the X and Z plane relative to the paper, and any components of these forces thereof. A practical example of such a member is a column of circular section, having for example a diameter to length ratio of 1:10, though other members of different section and proportion can obviously be used.

Thus the combination of two points of restraint yields a negligible K3 loading on the resonator in the torsional vibration mode whilst providing the structural strength and fluid sealing attributes required for wide utility.

FIG. 3 shows an analogous arrangement for a laterally vibrating system (tuning fork) though other similar arrangements can be anticipated where systems present nodal regions for separate sealing and structural members. The seal is located in a nodal region of the connection between the two inertial masses (in this example the tines of the fork and the support pin is located along a nodal line of the resonating structure. In this example the pin engages the base of the fork where a nodal line intersects the base. Such an arrangement can be stimulated into vibration by, for example, piezoelectric transducers disposed on the base of the fork and coupled into an appropriate sensing circuit.

In this embodiment, the pin (or column) will have a very high longitudinal rigidity, which is desirable to resist fluid pressure, compared to its lateral rigidity. The lateral stiffness of the tines of the fork should be substantially greater than the lateral stiffness of the support pin.

The casing is not as such essential to the invention in particular it need not include the wall engaged by the seal this wall may be the wall of a conduit or container in which the medium which is to be measured is contained or in which it flows the support for the resonator may be a frame which supports the pin and electromagnetic or other drive means and is adapted for securing to the wall of the conduit or container.

I claim:

1. A vibrational viscometer including:
   first and second distinct torsional resonators each comprising an inertial mass and a shaft;
   a nexus connecting the shafts of said first and second distinct torsional resonators, said first and second distinct torsional resonators being capable of vibration about a torsional axis in anti-phase, having a first vibrational node in the region of the nexus and at least a second vibrational node;
   a compliant support in the region of the first node, said compliant support at least partly surrounding said nexus; and
   a semi-rigid support in the region of the second node, said semi-rigid support comprising a support pin which is longitudinally rigid and torsionally compliant, said semi-rigid support being axially aligned with said torsional axis.

2. A vibrational viscometer according to as in claim 1 wherein said support pin extends between said first resonator and a casing.

3. A vibrational viscometer as in claim 1 wherein said support pin has a ratio of diameter to its length between said resonator and said casing of at least 1:10.

4. A vibrational viscometer including:
   a tuning fork resonator comprising two tines extending from a base;
   a casing;
   a compliant seal disposed between said casing and said base; and
   a support for said base, said support having a high longitudinal rigidity and a low lateral rigidity and comprising a pin disposed along a nodal line of the tuning fork resonator to extend between said base and said casing.

5. A vibrational viscometer as in claim 4 wherein said pin has a ratio of diameter to its length between said base and said casing of at least 1:10.

* * * * *